US005455240A

United States Patent [19]
Tuomanen et al.

[11] Patent Number: 5,455,240
[45] Date of Patent: Oct. 3, 1995

[54] MODULATORS OF PNEUMOCOCCAL ADHESION TO CELLULAR TARGETS INVOLVING THE PLATELET ACTIVATING FACTOR RECEPTOR, AND USES THEREOF

[75] Inventors: Elaine I. Tuomanen; Diana R. Cundell, both of New York, N.Y.; Norma P. Gerard, Dover, Mass.

[73] Assignees: The Rockefeller University, New York, N.Y.; Beth Israel Hospital Association, Boston, Mass.

[21] Appl. No.: 262,306

[22] Filed: Jun. 20, 1994

[51] Int. Cl.$^6$ .................................................. A61K 37/10
[52] U.S. Cl. ........................... 514/210; 514/8; 514/25; 536/4.1; 536/17.4; 536/17.6; 536/21; 424/122
[58] Field of Search .................................. 514/210, 231.5, 514/333; 536/4.1, 17.4

[56] References Cited

U.S. PATENT DOCUMENTS

| | | | |
|---|---|---|---|
| 5,132,286 | 7/1992 | Malabarba et al. | 514/8 |
| 5,304,556 | 4/1994 | Yamamoto et al. | 514/243 |
| 5,358,938 | 10/1994 | Cai et al. | 514/231.5 |

OTHER PUBLICATIONS

Cabellos et al., 1992, J. Clin. Invest. 90:612.
Tomasz and Saukkonen, 1989, Ped. Infect. Dis. J. 8:902–3.
Tuomanen et al., 1987, Am. Rev. Respir. Dis. 135:869–74.
Tuomanen et al., 1985, J. Infect. Dis. 151:535–40.
Tuomanen et al., 1985, J. Infect. Dis. 151:859–68.
Rozdzinski et al., 1993, J. Exp. Med. 178:917–24.
Geelen et al., 1993, Infect. Immun. 61:1538–43.
Tuomanen et al., 1988, J. Exp. Med. 168:267–77.
Krivan et al., 1988, Proc. Natl. Acad. Sci. USA 85:6157–61.
Andersson et al., 1983, J. Exp. Med. 158:559–70.
Hwang et al., 1989, Mol. Pharmacol. 35:48–58.
Hwang and Lam, 1991, LIPIDS 26:1148–53.
Wissner et al., 1986, J. Med. Chem. 29:328–33.
Gerard and Gerard, 1994, J. Immunol. 152:793–800.
Chao and Olson, 1993, Biochem. J. 292:617–629.
Kunz et al., 1992, J. Biol. Chem. 267:9101–6.
Dinarello and Wolff, 1993, N. Eng. J. Med. 328:106–113.
van de Kar et al., 1992, Blood 80:2755–64.

*Primary Examiner*—Arthur C. Prescott
*Attorney, Agent, or Firm*—Klauber & Jackson

[57] ABSTRACT

The present invention relates to compositions and methods for preventing pneumococcal infection. In particular, the invention relates to identification of the major reception for *Streptococcus pneumoniae* on activated human cells, and diagnostic and therapeutic compositions and methods based thereon. In particular, the invention relates to the discovery that platelet activating factor (PAF) receptor is an adhesive ligand for pneumococcal adherence to activated lung epithelial and venous endothelial (i.e., host) cells. Accordingly, the present invention is directed to a method for preventing or treating an infection with *Streptococcus pneumoniae* by administering an antagonist of platelet activating factor receptor. The invention further relates to recognition that adherence to activated cells also involves a carbohydrate ligand found on such activated cells. Thus, a method for inhibiting pneumococcal adherence may further comprise administering an amount of carbohydrate containing an N-acetyl-D-glucosamine motif. It has been found that resting lung epithelial and venous endothelial cells bear two classes of receptors containing different carbohydrate motifs. Thus, the invention further provides for administering an amount of a second carbohydrate selected from the group consisting of a carbohydrate containing a disaccharide N-acetyl-D-galactosamine β1-4Gal motif, a disaccharide N-acetyl-D-galactosamine β1-3Gal motif, and a mixture thereof. In addition, the invention provides pharmaceutical compositions comprising such agents that inhibit binding of pneumococci to human cells. In a specific example, platelet activating factor receptor antagonists and disaccharides are shown to inhibit binding of pneumococci to activated lung epithelial cells and venous endothelial cells, as well as cells transfected with the platelet activating factor receptor, in vitro.

27 Claims, 6 Drawing Sheets

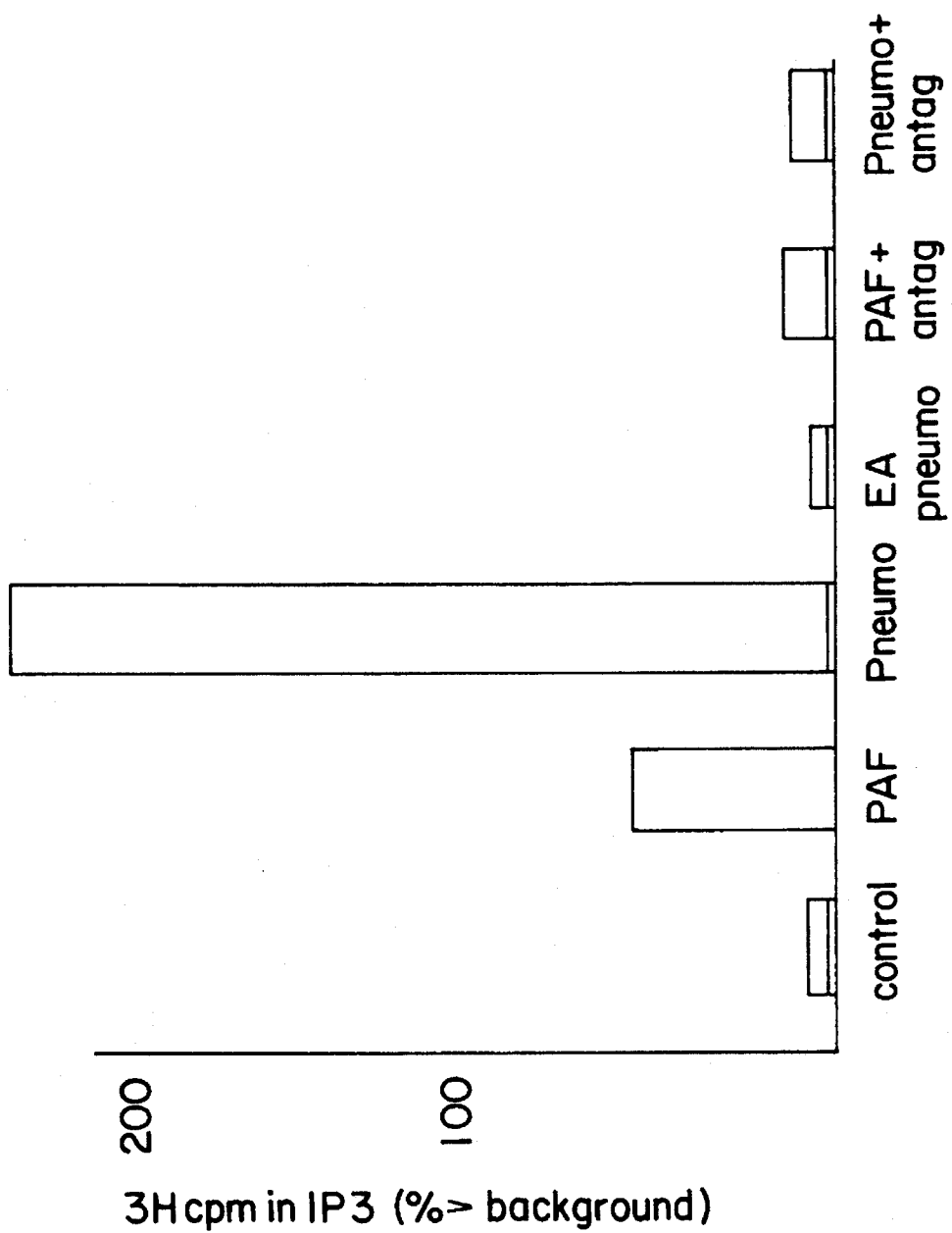

MODULATORS OF PNEUMOCOCCAL ADHESION TO CELLULAR TARGETS INVOLVING THE PLATELET ACTIVATING FACTOR RECEPTOR, AND USES THEREOF

The research leading to the present invention was supported in part by Grant No. AI-27913 from the National Institutes of Health. Accordingly, the Government has certain rights in the invention.

FIELD OF THE INVENTION

The present invention relates to compositions and methods for preventing pneumococcal infection. In particular, the invention relates to identification of the major reception for *Streptococcus pneumoniae* on activated human cells, and diagnostic and therapeutic compositions and methods based thereon.

BACKGROUND OF THE INVENTION

*Streptococcus pneumoniae* is a Gram positive pathogen which is a major cause of lobar pneumonia, sepsis and meningitis (Burman et at., 1985, Rev. Infect. Dis. 7: 133). This pathogenic bacterium is the most frequent cause of bacterial pneumonia in children of developing countries and accounts for up to 76% of cases in adults (Pennington, 1986, Am. Faro. Physician 33: 153; Johnston, 1991, Revs. Infect. Dis. 13 (Suppl. 6):S509; Musher, 1992, Clin. Infect. Dis. 14: 801). Pneumococci generally enter the host via the nasopharynx where they attach to epithelial cells and in some instances persist for several months (Anderson et al., 1981, Infect. Immun. 32: 311). In experimental models, progression to pneumonia results from spread of the pneumococci by aerosolization and conveyance from the nasopharynx down into the lower respiratory tract.

The early pneumonic lesion is characterized by fluid filled alveoli containing pneumococci, which are frequently seen to line the alveolar walls, a distribution suggestive of a specific interaction promoting retention in the alveolar space (Wood, 1941, J. Exp. Med. 73: 222). Pneumococci readily gain access to the blood circulation from the alveolar space, suggesting an aggressive capability to cross the vascular endothelial cells of the alveolar capillaries (Rake, 1936, J. Exp. Med. 63: 191).

Bacterial adherence to eukaryotic cells commonly involves specific bacterial proteins (adhesins) which recognize host cell glycoconjugates. Adherence of pneumococci to human oral epithelium is inhibited in the presence of the disaccharide N-acetyl-glucosamine-β1-3-galactose (GlcNAcβ1-3Gal) suggesting that this carbohydrate can serve as a receptor, perhaps relevant to nasopharyngeal carriage (Anderson et al., 1983, J. Exp. Med. 158: 559). It remains unknown precisely which cell type supports pneumococcal adherence in the alveolar space. Pneumococci have been reported to bind to purified glycoconjugates containing terminal or internal GalNAcβ1-4Gal, a structure prevalent in pulmonary secretions and lung tissue (Krivan et al., 1988, Proc. Natl. Acad. Sci. USA 85: 6157). This structure differs significantly in stereochemistry from that proposed for the nasopharyngeal receptor.

The identity of pneumococcal adhesions capable of mediating attachment to the nasopharynx, lung, and vascular endothelium is unknown. Consistent with the ability to readily cause experimental bacteremia, pneumococcal adherence to vascular endothelial cells has been shown to be dose-dependent, rapid and independent of capsular type (Geelen et at., 1993, Infec. Immunol. 61: 1538). Both cell-wall components and protein components contribute roughly equally to this association, but specific pneumococcal ligands remain to be identified (Tuomanen et at., 1985, J. Infect. Dis. 151: 859).

Invasive pneumococcal infection is characterized by particularly intense inflammation induced primarily by components of the pneumococcal cell wall (Tuomanen et al., 1985, J. Infect. Dis. 151: 535; Tuomanen et al., 1985, supra; Tuomanen et al., 1987, Am. Rev. Respir. Dis. 135: 869). Pneumococcal teichoic acid and lipoteichoic acid have the highest inflammatory capacity of all the cell wall components (Cabellos et al., 1992, J. Clin. Invest. 90: 612) and their bioactivity has been shown to be critically dependent on the presence of an unusual component: phosphorylcholine (Tomasz and Saukkonen, 1989, Paediatr. Infect. Dis. J. 8: 902). Phosphorylcholine is also the critical determinant of the biological activity of the inflammatory mediator, platelet activating factor (PAF) (Wissner et at., 1986, J. Med. Chem. 29: 329), suggesting a unique proinflammatory relationship between pneumococci and PAF in the pathogenesis of meningitis and pneumonia (Cabellos et al., supra).

As noted above, pneumococci adhere to glycoconjugates containing N-acetyl-D-galactosamine β1-4 galactose (GalNAcβ1-4Gal) or GalNAcβ1-3Gal either in purified form or presented on the surfaces of resting vascular endothelial and pulmonary type II epithelial cells (Krivan et al., 1988, Proc. Natl. Acad. Sci. USA 85: 6157). However, the local generation of inflammatory cytokines, such as tumor necrosis factor (TNF) and interleukin-1 (IL-1), during the course of infection can dramatically alter the presentation of potential receptors on cells (Rozdzinski et al., 1993, J. Exp. Med. 178: 917; van de Kar et at., 1992, Blood 11: 2725). For example, activation of vascular endothelial cells by TNF and IL-1 stimulates the synthesis of PAF (Bussolino et at., 1988, Biochim. Biophys. Acta 927: 43; Chao and Olson, 1993, Biochem. J. 292: 617; Zimmerman et al., 1992, Immunol. Today 13: 93–100) and increases expression of a variety of cell surface receptors including E-selectin (Rozdzinski et al., supra) and globotriosylceramide (van de Kar et al., supra).

Thus, there is a need in the art to identify ligands for bacterial adherence. There is a particular need in the art to identify such ligands on cells activated by inflammatory mediators. There is yet a further need to further characterize the role of pneumococci in inflammatory processes associated with pneumococcal infections.

The citation of references herein shall not be construed as an admission that such is prior art to the present invention.

SUMMARY OF THE INVENTION

The present invention relates to the discovery that platelet activating factor (PAF) receptor is a ligand for pneumococcal adherence to activated lung epithelial and venous endothelial (i.e., host) cells. It has also been found that pneumococcal binding to the PAF receptor activates the receptor, which may in turn increase inflammation. Accordingly, the present invention is directed to a method for preventing or treating an infection with *Streptococcus pneumoniae* comprising administering to a subject believed to be in need of such treatment an amount of an antagonist of platelet activating factor receptor effective to inhibit binding of *S. pneumoniae* to host cells, and to inhibit activation of the PAF receptor subsequent to such binding. More preferably, the PAF receptor antagonist is effective to elute (i.e., remove or detach) adherent pneumococci from host cells. In a specific embodiment, the antagonist of platelet activating factor receptor is selected from the group consisting of L659,989, L652,731 WEB 2086, kadsurenone, and FR72112; additional antagonists are described in Hwang and Lam, 1991, Lipids 26: 1148–53, Hwang et at., 1989, Mol. Pharmacol. 35: 48–58, which are specifically incorporated herein by reference in their entirety.

Inhibition of binding of pneumococci to the PAF receptor has important implications for preventing migration of pneumococci across epithelial and endothelial tissues. Migration of bacteria from the nasopharynx and lung into the blood can lead to a systemic bacterial infection, resulting in bacteremia, sepsis, and meningitis. Activation via the PAF receptor further complicates these pathological pathways, in particular, by generating or exacerbating inflammation leading to increased vascular permeability (see, e.g., Tuomanen et al., 1985, J. Infect. Dis. 151: 535–540).

The invention further relates to recognition that adherence to activated cells also involves a carbohydrate ligand found on such activated cells. Thus, a method for inhibiting pneumococcal adherence may comprise administering an amount of carbohydrate containing an N-acetyl-D-glucosamine motif effective to inhibit binding of S. pneumoniae to host cells. In a specific embodiment, the carbohydrate is N-acetyl-D-glucosamine. Preferably, such a method is used in conjunction with administration of a PAF receptor antagonist.

It has been found that resting lung epithelial and venous endothelial cells bear two classes of receptors containing different carbohydrate motifs. Thus, the invention further provides for administering an amount of a second carbohydrate selected from the group consisting of a carbohydrate containing a disaccharide N-acetyl-D-galactosamine β1-4Gal motif, a disaccharide containing a N-acetyl-D-galactosamine β1-3Gal motif, and a mixture thereof, effective to inhibit binding of S. pneumoniae to host cells. In a specific embodiment, the second carbohydrate is selected from the group consisting of forssman glycolipid, globoside, asialo-GM1 and asialo-GM2.

The method for inhibiting binding of pneumococci to host cells may further comprise administering an amount of a carbohydrate selected from the group consisting of mannose, N-acetyl-galactose, mannose-D-mannose, and methyl-α-D-mannopyranoside effective to inhibit binding of S. pneumoniae to host cells.

In a preferred aspect, where carbohydrates are used in the methods of the invention, the carbohydrate or carbohydrates are multivalent.

In one embodiment, the administering comprises atomizing and inhaling. For example, atomization can be performed by nebulizing. Alternatively, the invention provides for parenteral administration, e.g., injecting intravenously. In yet a further embodiment, a PAF receptor antagonist can be administered orally.

The invention further recognizes that PAF receptor expression increases in host cells activated with inflammatory mediators, such as the cytokines tumor necrosis factor (TNF) and interleukin-1 (IL-1). Pneumococci directly stimulate inflammatory responses, in particular by the activity of the pneumococcal wall components teichoic acid and lipoteichoic acid. Thus, the invention further contemplates administering an inhibitor of inflammation effective to inhibit expression of platelet activating factor receptor. In a specific aspect, the inhibitor of inflammation is selected from the group consisting of a neutralizing antibody to tumor necrosis factor, a neutralizing soluble tumor necrosis factor receptor, a neutralizing antibody to interleukin-1, and a neutralizing soluble interleukin-1 receptor.

In addition to therapeutic methods, the invention provides a pharmaceutical composition comprising an amount of a platelet activating factor receptor antagonist effective to inhibit binding of S. pneumoniae to host cells, an amount of a carbohydrate containing an N-acetyl-D-glucosamine motif effective to inhibit binding of S. pneumoniae to host cells, and a pharmaceutically acceptable carrier. The antagonist of platelet activating factor receptor may be selected from the group consisting of L659,989, L652,731, kadsurenone, FR72112, and WEB 2086; the carbohydrate may be N-acetyl-D-glucosamine.

In a further embodiment, the pharmaceutical composition comprises an amount of a second carbohydrate selected from the group consisting of a carbohydrate containing a disaccharide N-acetyl-D-galactosamine β1-3Gal motif and a carbohydrate containing a disaccharide N-acetyl-D-galactosamine β1-4Gal motif effective to inhibit binding of S. pneumoniae to host cells. The second carbohydrate may be selected from the group consisting of forssman glycolipid, globoside, asialo-GM1 and asialo-GM2.

In yet a further embodiment, the pharmaceutical composition comprises an amount of a carbohydrate selected from the group consisting of mannose, N-acetylgalactose, mannose-D-mannose, and methyl-α-D-mannopyranoside effective to inhibit binding of S. pneumoniae to host cells.

Preferably, in the pharmaceutical compositions containing a carbohydrate or carbohydrates, the carbohydrate or carbohydrates are multivalent.

In a particular aspect, the invention specifically provides a pharmaceutical composition in which the pharmaceutical composition is an aerosol formulation, which formulation contains a dispersant. For example, the dispersant may be a surfactant. In one embodiment, the pharmaceutical composition is a dry powder aerosol formulation, in which the antagonist of PAF receptor, and, if present, carbohydrate or carbohydrates, are present in finely divided powder. The dry powder aerosol formulation may further comprise a bulking agent. In another embodiment, the pharmaceutical composition is a liquid aerosol formulation further comprising a pharmaceutically acceptable diluent. The diluent may be selected from the group consisting of sterile water, saline, buffered saline, and dextrose solution.

In a specific aspect, the invention provides an pharmaceutical composition in an aerosol formulation comprising an antagonist of PAF receptor. Such a formulation may be a dry powder aerosol formulation, or a liquid aerosol formulation. Such an aerosol formulation may further comprise a carbohydrate containing an N-acetyl-D-glucosamine motif. In further embodiments, the composition may comprise a second carbohydrate selected from the group consisting of a carbohydrate containing a disaccharide N-acetyl-D-galactosamine β1-3Gal motif and a carbohydrate containing a disaccharide N-acetyl-D-galactosamine β1-4Gal motif effective to inhibit binding of S. pneumoniae to host cells.

It is a primary object of the invention to provide a method and associated compositions for inhibiting pneumococcal adherence to activated host cells, in particular, lung epithelial cells and venous endothelial cells.

It is a further object of the invention to inhibit pneumococcal activation of the PAF receptor.

These, and other objects of the present invention will be more completely understood by reference to the drawings and the following detailed description.

BRIEF DESCRIPTION OF THE DRAWINGS

FIG. 6. Pneumococci activate the PAF receptor. COS cells in a monolayer were treated with control, platelet activating factor (100 mM), pneumococci ($10^8$ bacteria/ml), ethanolamine-cultured pneumococci ($10^8$ bacteria/ml), PAF+ L659, 989, and pneumococci+L659,989. Activation was measured by detecting the level of incorporation of $^3H$ in inositoltriphosphate, which is reported as the percentage above background.

DETAILED DESCRIPTION OF THE INVENTION

Figure 1A:
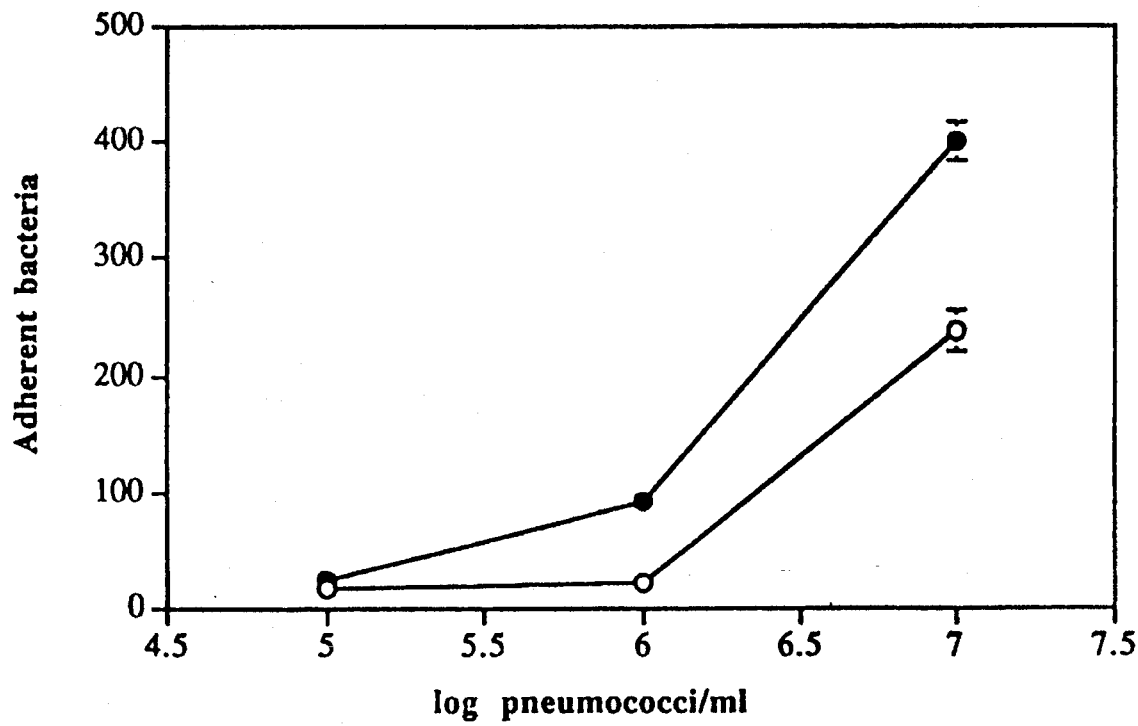
FIG. 1. Adherence of pneumococci to cytokine-stimulated human cultured type II pneumocytes (A) and vascular endothelial cells (B). Monolayers in 60 well Terasaki dishes were stimulated with IL-1α (type II lung cells; 5 ng/ml, 4 h at 37° C.; Rozdzinski et al., 1993, J. Exp. Med. 178: 917) and TNFα (vascular endothelial cells; 10 ng/ml, 3 h at 37° C.; Elias et al., 1990, Am. J. Respir. Cell. Mol. Biol. 3: 13). Pneumococci R6 and AII were cultured for 18 h on trypticase soy agar containing 3% sheep blood, labelled with fluorescein isothiocyanate and adjusted to $10^5$–$10^7$ cfu/ml (Geelen et al., 1993, Infect. Immun. 61: 1538), and co-incubated with the monolayers. Control adherence in the absence of cytokine is indicated by a hatched line (-----). Bacteria adherent to cytokine-stimulated (●) and resting (○) monolayers were determined as the number of attached bacteria per 100 lung or endothelial cells. Results are the means ±SD for duplicate wells in at least six independent experiments.
Figure 1B:
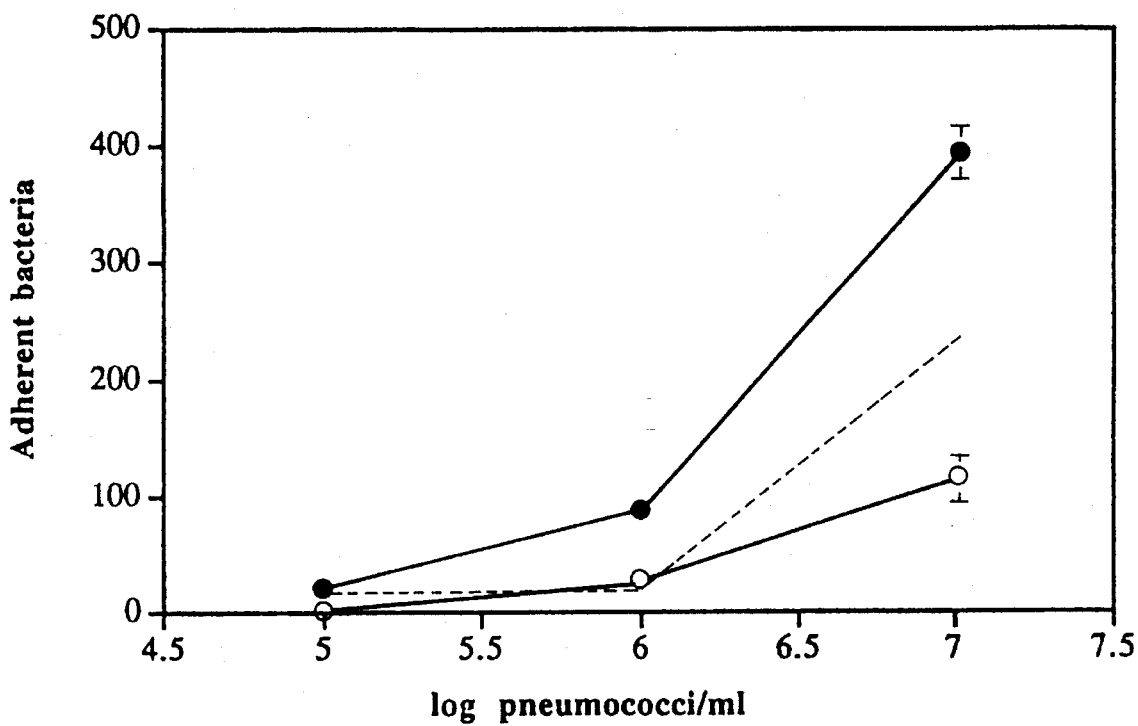
Figure 2A:
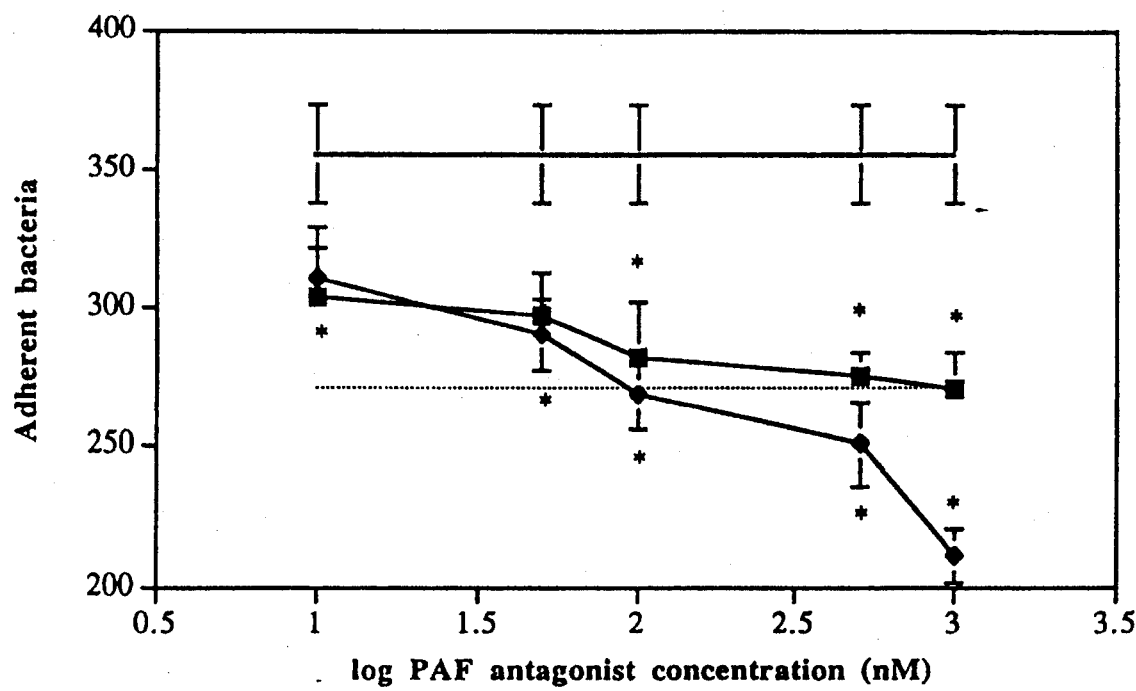
FIG. 2. Effect of PAF receptor antagonists on pneumococcal adherence to IL-1α-stimulated cultured human type II lung cells (A) and TNFα-stimulated vascular endothelial cells (B). Cytokine stimulated monolayers were incubated (10 min, 37° C.) with either albumin buffer (—) or increasing concentrations of the PAF receptor antagonists L659,989 (♦) and WEB 2086 (■) and R6 pneumococci ($10^7$ cfu/ml) allowed to adhere to the monolayers for 30 min at 37° C. Control adherence in the absence of cytokine stimulation is indicated by a horizontal dotted line (------). Adherent bacteria were determined as the number of attached bacteria per 100 lung or endothelial cells. Results are the means ±SD for duplicate wells in at least six independent experiments. $*p<0.05$ compared with cytokine-stimulation in the absence of antagonists.
Figure 2B:
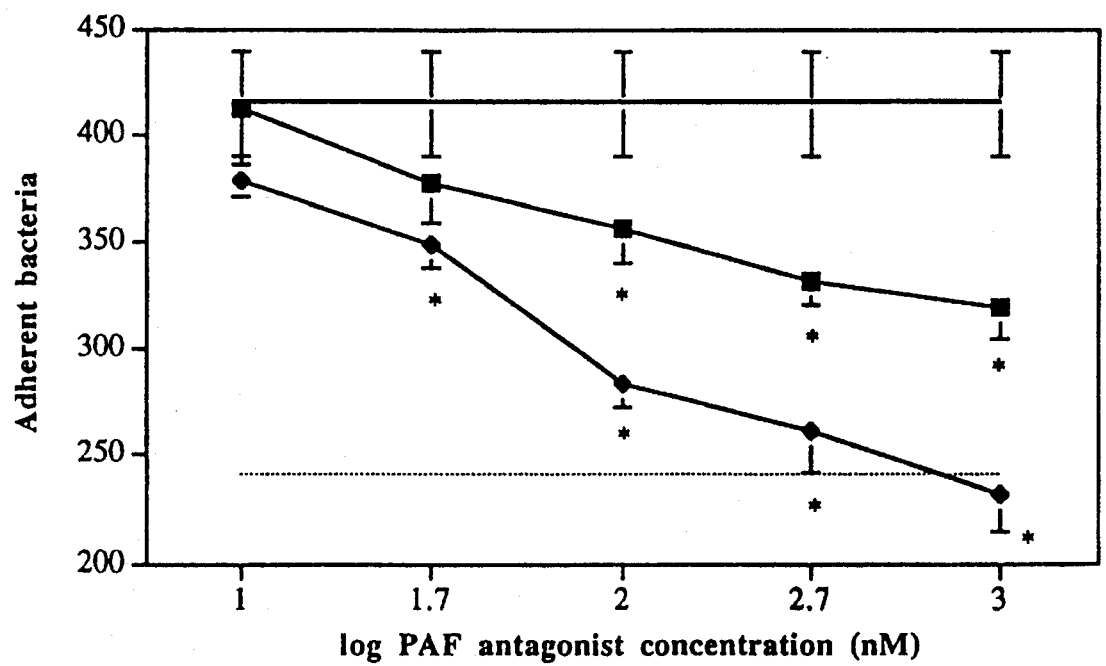

It has been known that pneumococci adhere to and activate pulmonary epithelial cells and vascular endothelial cells during the course of pneumonia and bacteremia. Cytokine activation of human vein endothelial cells and type II lung cells results in greatly enhanced pneumococcal adherence. The present invention is based, in part, on the unexpected discovery that enhanced binding of pneumococci to activated pulmonary epithelium and vascular endothelium was eliminated in the presence of platelet activating factor (PAF) receptor antagonists. In one example, upon transfection with the PAF receptor, human kidney epithelial cells gained the ability to support pneumococcal adherence consistent with specific receptor activity. It was also observed that the presence of PAF, GlcNAc, PAF receptor antagonists, or site specific mutation to eliminate the single glycosylation site on the transfected PAF receptor resulted in a dramatic reduction of pneumococcal binding. Adherence to activated type II pneumocytes, vascular endothelium and transfected cells depended on phosphorylcholine on the bacterial surface indicating that this unique component of the teichoic acid, like the phosphorylcholine moiety in PAF, targets pneumococci to the PAF receptor.

Accordingly, the present invention relates to compositions and methods for treating or preventing infection with S. pneumoniae. As summarized above, the present invention is based on the discovery that pneumococci recognize, bind to and activate platelet activating factor receptor, which is expressed by lung epithelial and venous endothelial cells activated with inflammatory mediators, such as tumor necrosis factor (TNF) and interleukin-1 (IL-1). The invention is further based on the discovery that activation of such cells is accompanied by expression of a GlcNAc carbohydrate moiety, which also mediates pneumococcal adherence, a property of GlcNAc not previously recognized prior to the present invention. The invention further relates to recognition that pneumococci associate with at least two other different carbohydrate motifs, one of which has only recently been recognized. This latter aspect of the invention is more fully developed in copending application Ser. No. 08/254,577, Attorney Docket No. 600-1-084, filed Jun. 6, 1994, by Tuomanen and Curtdell, entitled "MODULATORS OF PNEUMOCOCCAL ADHERENCE TO PULMONARY AND VASCULAR CELLS AND DIAGNOSTIC AND THERAPEUTIC APPLICATIONS," hereinafter "Tuomanen and Cundell," which is specifically incorporated herein by reference in its entirety. In specific embodiments, the invention provides for inhibiting adhesion of pneumococci, or eluting adherent pneumococci, from lung epithelial cells and from venous endothelial cells.

The present inventors have discovered that platelet activating factor (PAF) receptor interacts with a phosphorylcholine entity in pneumococci—the teichoic acid and lipoteichoic acid moieties of the bacterial cell wall. The inventors have further discovered a role for GalNacβ1-3Gal-containing carbohydrates and the carbohydrate group on PAF receptor in the adhesion of pneumococci to host cells, such as lung epithelial cells and vascular endothelial cells. Furthermore, the inventors have found that internalization of bacteria is associated with binding to the PAF receptor. This internalization appears to afford bacteria a route of migration into or across endothelium and epithelium, resulting in systemic infection, which can lead to bacteremia, sepsis, and meningitis. Thus, the instant invention provides a potent tool, effective against antibiotic resistant bacteria as well as antibiotic sensitive bacteria, for preventing pneumococcal infection and pathogenesis.

To provide a better understanding of the invention, definitions for certain terms are provided below; aspects of the invention—PAF receptor antagonists; inhibitors of PAF receptor expression; carbohydrates; therapeutic compositions and methods; and Examples are also presented.

As the invention relates in part to conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984).

A composition comprising "A" (where "A" is a single molecule, such as a PAF receptor antagonist, protein, carbohydrate, etc.) is substantially free of "B" (where "B" comprises one or more contaminating molecules) when at least about 75% by weight of the components of the composition (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

As used herein, the term "host cell" refers to a cell capable of colonization by pneumococci, for example lung epithelial cells and venous endothelial cells.

As used herein, the term "pulmonary administration" refers to administration of a formulation of the invention into the lungs by inhalation.

As used herein, the term "inhalation" refers to intake of air to the alveoli. In specific examples, intake can occur by self-administration of a formulation of the invention while inhaling, or by administration via a respirator, e.g., to an patient on a respirator. The term "inhalation" used with respect to a formulation of the invention is synonymous with "pulmonary administration."

As used herein, the term "aerosol" refers to suspension in the air. In particular, aerosol refers to the particalization of a formulation of the invention and its suspension in the air. According to the present invention, an aerosol formulation is a formulation comprising an antagonist of PAF receptor, and also possibly a carbohydrate, that is aerosolized, i.e., atomized and suspended in the air, for inhalation or pulmonary administration.

As used herein, the term "parenteral" refers to introduction of an antagonist of platelet activating factor, and possibly a carbohydrate, that inhibits binding or adherence of pneumococci to mammalian cells into the body, and in particular, oral, intravenous (i.v.), intraarterial (i.a.), intraperitoneal (i.p.), intramuscular (i.m.), intraventricular, and subcutaneous (s.c.) routes. Preferably, the route is intravenous or oral.

As used herein, the term "systemic" refers to a disease or disorder, or original site of injury distant to the lung or involving the entire body of the organism. The term "local" therefore is used herein with respect to the lung. Thus, a systemic infection is one in which *S. pneumonia* are found in the blood, and can lead to bacteremia, sepsis, and meningitis. A local infection is one in which the pneumococci have migrated only as far as the lung, and can lead to pneumonia.

The compositions of the invention, or the administration of a composition, can be used to protect or treat an animal subject from infection of *S. pneumoniae.* Thus, a composition of the invention can be used in birds, such as chickens, turkeys, and pets; and in mammals, preferably a human, although the compositions of the invention are contemplated for use in other mammalian species, including but not limited to domesticated animals (canine and feline); farm animals (bovine, ovine, equine, caprine, porcine, and the like); rodents; and undomesticated mammals.

Antagonists of PAF Receptor

In its primary aspect, the present invention relates to methods for inhibiting or preventing infection and PAF receptor activation with pneumococcus, comprising inhibiting binding of pneumococci to PAF receptor, or eluting adherent pneumococci from PAF receptor, or both.

In one aspect of the invention, antagonists of PAF receptor can be used to inhibit such binding or elute adherent bacteria. As used herein, the term "antagonist of platelet activating factor receptor" refers to a molecule that competitively inhibits binding of pneumococci to platelet activating factor receptor. Preferably, the agonist does not itself activate PAF receptor, however, such molecules are not excluded where they may effectively inhibit adhesion of pneumococci to the PAF receptor. For example, PAF itself competitively inhibits binding of pneumococci to the receptor. Such antagonists, or competitive inhibitors of binding to PAF receptor, include but are not limited to molecules containing phosphorylcholine (see, e.g., Tence et al., 1983, in *Platelet-Activating Factor and Structurally Related Ether-Lipids,* INSERM Symposium No. 23, J. Benveniste and B. Arnoux (eds.), Elsevier Science Publishers: Amsterdam, pp. 41–48). More particularly, a PAF receptor antagonist may be selected from the group consisting of L659,989, L652,731, WEB 2086, kadsurenone, and FR72112, e.g., Hwang and Lain, 1991 Lipids 26: 1148–53; Hwang et al., 1989, Mol. Pharmacol. 35: 48–58, which are incorporated herein by reference. In specific examples, infra, antagonists of PAF receptor include, but are not limited to, L659,989 (available from Merck & Co., Rahway, N.J.) and WEB 2086 (available from Boehringer Ingleheim, Indianapolis, Ind.)

Inhibitors of PAF Receptor Expression

In a further embodiment, administration of an inhibitor of PAF receptor activation to a subject can be used to inhibit binding and internalization of bacteria. As used herein, an inhibitor of PAF receptor activation may be any immunosuppressive agent, including but not limited to non-steroidal anti-inflammatory agents (such as, but not limited to, aspirin, salicylic acid, ibuprofin, etc.), steroidal anti-inflammatory agents (such as cortisone, etc.), and inhibitors of inflammatory cytokines, such as TNF and IL-1.

As used herein, the term "inhibitors of inflammatory cytokines" refers to molecules that neutralize the activity of inflammatory cytokines. Such molecules can be antibodies that bind to the cytokine, and inhibit the activity of the cytokine, whether directly (by steric interference with binding of the cytokine to its receptor) or indirectly (by providing for rapid clearance of the cytokine via antibody-mediated clearance pathways) (see e.g., Dinarello and Wolff, 1993, New Engl. J. Med. 328: 106–113). Such antibodies can be obtained from commercial or other sources, or can be prepared. Such antibodies include but are not limited to polyclonal, monoclonal, chimeric, single chain, Fab fragments, and an Fab expression library. Accordingly, as used herein, the term "antibody" broadly relates to immunoglobulin or antigen-binding fragments thereof. Alternatively, soluble receptors for inflammatory cytokines can be used to inhibit the activity of the cytokines (see, Dinarello and Wolff, supra).

Carbohydrate Motifs That Bind to Pneumococci

In a further aspect, the present invention relates to the identification of the carbohydrate motifs that mediate adherence of pneumococci to host cells, in particular lung epithelial cells (Type II lung cells), and venous endothelial cells. In particular, the inventors herein have discovered that stimulation of the host cells to which pneumococci bind with inflammatory cytokines, such as tumor necrosis factor (TNF), interleukin-1 (IL-1), etc., induces a previously unknown carbohydrate specificity: N-acetyl-D-glucosamine (GlcNAc). It has also been found that this GlcNAc sugar specificity is associated with the GalNAcβ1-3Gal receptor population. Thus, a composition comprising a carbohydrate with the GalNAcβ1-3Gal motif and the GlcNAc motif (both motifs can be found on the same oligosaccharide, or on two different oligosaccharides) can be used to prevent adherence of pneumococci to, or elute adherent pneumococci from, host cells.

Thus, as used herein, the term "pneumococcal carbohydrate binding motif" refers to the structure of a carbohydrate that is recognized by the pneumococcal bacterial adhesion complex, or the minimum receptor unit for such binding or adhesion. It is well known that a carbohydrate (also termed oligosaccharide and saccharide) on a glycoprotein can be a highly complex structure formed by a set of monosaccharide (sugar) subunits arranged in a variety of linkages (see, e.g., Darnell et al., *Molecular Cell Biology,* Scientific American Books, 1986, pp. 957–964). The motif of the present invention is the minimum receptor unit, i.e., the minimum structure capable of binding with pneumococci, regardless of the "decoration" (additional saccharide subunits) found on the compound. Thus, the carbohydrate motif to which pneumococci bind can be located in a complex oligosaccharide, or may be the simplest possible oligosaccharide having the motif structure. Furthermore, a motif can be a derivative of the specific saccharide groups shown herein to mediate pneumococcal binding. A functional definition of a motif of the invention is that it can demonstrate pneumococcal binding and elution properties as described in the Examples herein.

As used herein, the term "carbohydrate" refers both to compounds containing saccharide subunits, and to such compounds associated or conjugated with a polymer as described herein.

In yet a further aspect, the invention takes advantage of the identification of a carbohydrate motif to which pneumococci bind that has not previously been known to mediate pneumococci binding. This motif contains a disaccharide N-acetyl-D-galactosamine β1-3Gal group (GalNAcβ1-3Gal). This motif may be, but need not be, linked to a mannose. Examples of carbohydrates that contain this motif include, but are not limited to, forssman glycolipid, globoside, etc.

It has been discovered that quantitative or nearly quantitative elution of adherent pneumococci from host cells can be achieved by contacting pneumococci with the GalNAcβ1-3Gal motif and a second motif, to which pneumococci were previously known to adhere. This second motif is a carbohydrate containing a disaccharide N-acetyl-D-galactosamine β1-4Gal group (GalNAcβ1-4Gal). This motif may be, but need not be, linked to a mannose. Examples of carbohydrates that contain this second motif include, but are not limited to, asialo-GM1, asialo-GM2, etc. Quantitative elution of pneumococci from unstimulated lung epithelial cells (Type II lung cells) and venous endothelial cells can be achieved by contacting these cells with a composition containing carbohydrates having both motifs (Tuomanen and Cundell, supra).

In the most preferred embodiment, a composition comprising carbohydrates that represent all three motifs can be used in conjunction with a PAF receptor antagonist. Such a composition is particularly desirable to treat an early stage, ongoing infection, in which the immune system has been activated and inflammatory mediators have been released. Preferably, such a composition is administered prior to internalization of pneumococci, and migration of the pneumococci into the blood.

The invention contemplates including additional carbohydrate moieties that have been found to interfere with binding or adherence of pneumococci with host cells. Examples of such carbohydrates include, but are not limited to, mannose, N-acetyl-D-galactosamine, mannose-D-mannose, and methyl-α-D-mannopyranoside.

The present invention further contemplates use of multivalent carbohydrates or carbohydrate-containing structures to increase the potency of the drug. In one embodiment, one motif is found in multiple copies on a compound for use in the invention. In another embodiment, more than one motif is found in single or multiple copies on a compound for use in the invention. Multivalent carbohydrates can be prepared by preparing a branching complex carbohydrate, which conceptually resembles a tree or brush in which each branch or bristle contains a pneumococcal binding motif. Alternatively, monovalent carbohydrates can be associated covalently or non-covalently with a polymer (e.g., Langer et al., International Patent Publication No. WO 94/03184, published Feb. 17, 1994, which is specifically incorporated herein by reference). Suitable polymers include, but are not limited to, a protein, polylysine, dextran, a glycosaminoglycan, cyclodextrin, agarose, SEPHAROSE, and polyacrylamide.

Carbohydrates with pneumococcal binding motifs according to the invention can be obtained from any source. For example, such carbohydrates can be obtained from commercial sources. Alternatively, the carbohydrates can be prepared synthetically, using known chemical or enzymatic processes. Glycosyltransferase enzymes for synthesis of a carbohydrate (i.e., saccharide) that contains a pneumococcal binding motif can be prepared as described in International Patent Publication No. WO 93/13198 by Roth (published Jul. 8, 1993), which is incorporated herein by reference. Glycosyltransferase-catalyzed preparation of saccharide compositions has also been described (Roth, U.S. Pat. No. 5,180,674, issued Jan. 19, 1993, and International Patent Publication No. 91/16449, published Oct. 31, 1991), as has an apparatus for preparing such compositions (Roth, U.S. Pat. No. 5,288,637, issued Feb. 22, 1994) (each of these references is specifically incorporated herein by reference in its entirety).

Therapeutic Compositions and Methods

The present invention contemplates formulations comprising a PAF receptor antagonist, preferably with a carbohydrate containing a pneumococcal binding motif as described above for pulmonary or parenteral, especially i.v. or oral, administration for the prevention and treatment of pneumococcal infection, and resulting disease conditions including, but not limited to, bacteremia, meningitis, and pneumonia. Hereinafter, for convenience sake, the term "carbohydrate" in the singular or plural form should be interpreted to mean a carbohydrate containing a pneumococcal binding motif, unless another meaning is specifically provided.

Accordingly, the present invention provides pharmaceutical compositions comprising a PAF receptor antagonist, preferably with one or more carbohydrates containing a pneumococcal binding motif and a pharmaceutically acceptable carrier or excipient, as defined above.

Since certain PAF receptor antagonists, such as L659,989, are orally active, the invention contemplates oral administration of such compounds (see Hwang and Lam, 1991, Lipids 26: 1148–53).

For the treatment of a nascent pneumococcal infection or a systemic infection, a therapeutic composition of the invention can be administered by inhalation, to prevent colonization of lung epithelial cells leading to infection, or to elute adherent bacteria from lung epithelial cells. Pulmonary administration is an effective mode of administration for the bloodstream as well, since drugs pass from the alveoli into the capillaries readily. Moreover since systemic pneumococcal infections generally begin with colonization of lung epithelial cells, administration of a therapeutic agent via the lungs is a rational route to treat the infection. Similarly, it is also possible for a drug administered parenterally, e.g., i.v., to cross from the capillaries to the alveoli. Accordingly, the present invention contemplates parenteral administration of a pharmaceutical composition of the invention, in particular i.v. administration, for treatment of both systemic and lung (local) pneumococcal infections.

Accordingly, a wide variety of devices that are designed for the delivery of pharmaceutical compositions and therapeutic formulations to the respiratory tract or parenterally can be used in this aspect of the invention. The preferred route of pulmonary administration of the present invention is in the aerosol or inhaled form. The PAF receptor antagonist, preferably with a carbohydrate or carbohydrates of the present invention, combined with a dispersing agent, or dispersant, can be administered in an aerosol formulation as a dry powder or in a solution or suspension with a diluent. However, as mentioned above, the composition of the invention can also be administered parenterally.

As used herein, the term "dispersant" refers to a agent that assists aerosolization of the PAF receptor antagonist, preferably with a carbohydrate or absorption of this agent in lung tissue, or both. Preferably the dispersant is pharmaceutically acceptable. For example, surfactant that are generally used in the art to reduce surface induced aggregation of the PAF receptor antagonists, or PAF receptor antagonist and carbohydrates, caused by atomization of the solution forming the liquid aerosol may be used. Non-limiting examples of such surfactant are surfactant such as polyoxyethylene fatty acid esters and alcohols, and polyoxyethylene sorbitan fatty acid esters. Amounts of surfactant used will vary, being generally within the range or 0.001 and 4% by weight of the formulation. Suitable surfactant are well known in the art, and can be selected on the basis of desired properties, depending on the specific formulation, concentration of PAF receptor, and, if present, carbohydrate or carbohydrates, diluent (in a liquid formulation) or form of powder (in a dry powder formulation), etc.

Moreover, depending on the choice of the PAF receptor antagonist, and, if present, carbohydrate or carbohydrates (e.g., disaccharide or complex oligosaccharide), the desired therapeutic effect, the quality of the lung tissue (e.g., diseased or healthy lungs), and numerous other factors, the liquid or dry formulations can comprise additional components, as discussed further below.

The liquid aerosol formulations contain the PAF receptor antagonist, and, if present, carbohydrate or carbohydrates and a dispersing agent in a physiologically acceptable diluent. The dry powder aerosol formulations of the present invention consist of a finely divided solid form of the PAF receptor antagonist, and, if present, carbohydrate or carbohydrates, and a dispersing agent. The parenteral formulations contain the PAF receptor antagonist, and, if present, carbohydrate or carbohydrates, in a suitable carrier for injection.

With either the liquid or dry powder aerosol formulation, the formulation must be aerosolized. That is, it must be broken down into liquid or solid particles in order to ensure that the aerosolized dose actually reaches the alveoli. In general the mass median dynamic diameter will be 5 micrometers or less in order to ensure that the drug particles reach the lung alveoli (Wearley, L. L., 1991, 1991, Crit. Rev. in Ther. Drug Carder Systems 8: 333). The term "aerosol particle" is used herein to describe the liquid or solid particle suitable for pulmonary administration, i.e., that will reach the alveoli. Other considerations such as construction of the delivery device, additional components in the formulation and particle characteristics are important. These aspects of pulmonary administration of a drug are well known in the art, and manipulation of formulations, aerosolization means and construction of a delivery device require at most routine experimentation by one of ordinary skill in the art.

With regard to construction of the delivery device, any form of aerosolization known in the art, including but not limited to nebulization, atomization or pump aerosolization of a liquid formulation, and aerosolization of a dry powder formulation, can be used in the practice of the invention. Often, the aerosolization of a liquid or a dry powder formulation will require a propellent. The propellent may be any propellant generally used in the art. Specific non-limiting examples of such useful propellants are a chlorofluorocarbon, a hydrofluorocarbon, a hydochlorofluorocarbon, or a hydrocarbon, including triflouromethane, dichlorodifluoromethane, dichlorotetrafluoroethanol, and 1,1,1,2-tetrafluoroethane, or combinations thereof.

In a particular aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

Once the PAF receptor antagonist, and, if present, carbohydrate or carbohydrates reach the lung by inhalation, a number of formulation-dependent factors effect the binding activity. It will be appreciated that in treating a systemic pneumococcal infection, that requires circulatory levels of the PAF receptor antagonist, and, if present, carbohydrate or carbohydrates, such factors as aerosol particle size, aerosol particle shape, the presence or absence of lung disease or emboli that may affect the absorption of the PAF receptor antagonist, and, if present, carbohydrates, pH of the lungs or the pharmaceutical carrier, etc. For each of the formulations described herein, certain lubricators, absorption enhancers, stabilizers or suspending agents may be appropriate. The choice of these additional agents will vary depending on the goal. It will be appreciated that in instances where local delivery of the PAF receptor antagonist, and, if present, carbohydrate or carbohydrates, is desired or sought, such variables as absorption enhancement will be less critical.

In a further embodiment, an aerosol or parenteral formulation of the present invention can include other active ingredients in addition to the PAF receptor antagonist, and, if present, carbohydrate or carbohydrates. In a preferred embodiment, such active ingredients are those used for the treatment of lung disorders. For example, such additional active ingredients include, but are not limited to, bronchodilators, antihistamines, epinephrine, and the like, which are useful in the treatment of pulmonary conditions. In a preferred embodiment, the additional active ingredient can be an antibiotic, e.g., for the treatment of pneumonia. In a preferred embodiment, the antibiotic is pentamidine.

While in a preferred aspect the compositions of the present invention are administered in conjunction with antibiotics, it is a particular advantage of the present invention that it provides a strategy for treating antibiotic resistant pneumococcus. This is an important consideration in view of the recent increase in antibiotic resistance among virulent bacteria, a phenomenon that is of grave public health concern.

Recognition that pneumococci activate the PAF receptor provides added incentive for using antagonists of PAF receptor in the treatment of pneumococcal infection. The use of such inhibitors can not only prevent colonization and internalization of the bacteria, but can also alleviate the inflammatory response associated with exposure to the bacteria.

In general, the PAF receptor antagonist, and, if present, carbohydrate or carbohydrates of the present invention, are introduced into the subject in the aerosol or parenteral form in an amount between 0.01 mg per kg body weight of the mammal up to about 100 mg per kg body weight of said mammal. In a specific embodiment, the dosage is dosage per day. One of ordinary skill in the art can readily determine a volume or weight of aerosol corresponding to this dosage based on the concentration of PAF receptor antagonist, and, if present, carbohydrate or carbohydrates, in an aerosol or parentera formulation of the invention; alternatively, one can prepare an aerosol formulation with the appropriate dosage of PAF receptor antagonist, and, if present, carbohydrate or carbohydrates, in the volume to be administered, as is readily appreciated by one of ordinary skill in the art. It is also clear that the dosage will be higher in the case of inhalation therapy for a systemic pneumococcal infection, and may be lower for treating an infection of the lung only, since the local concentration of PAF receptor antagonist, and, if present, carbohydrate or carbohydrates, in the lung will be much higher with pulmonary administration. It is an advantage of the present invention that administration of a PAF receptor antagonist, and, if present, carbohydrate or carbohydrates, directly to the lung allows targeted drug delivery, thus limiting both cost and unwanted side effects.

The formulation may be administered in a single dose or in multiple doses depending on the severity of the infection or need for prophylaxis. For example, when administered to a subject on a respirator as protection against pneumococcal infection (a common consequence of long-term treatment on a respirator), less of the composition may be effective. If an infection commences, more of the composition can be provided to facilitate elution of adherent bacteria as well as prevent adhesion and colonization by resident bacteria. It will be appreciated by one of skill in the art the exact amount of prophylactic or therapeutic formulation to be used will depend on the stage and severity of the disease, the physical condition of the subject, and a number of other factors, which can be readily determined by the skilled physician (see, e.g., Langer et al., International Patent Publication No. WO 9403184, published Feb. 17, 1994, which is specifically incorporated herein by reference).

Systems of aerosol delivery, such as the pressurized metered dose inhaler and the dry powder inhaler are disclosed in Newman, S. P., *Aerosols and the Lung,* Clarke, S. W. and Davia, D. editors, pp. 197–22 and can be used in connection with the present invention.

Liquid Aerosol Formulations

The present invention provides liquid aerosol formulations and dosage forms for use in treating subjects suffering from or in danger of acquiring a pneumococcal infection. In general such dosage forms contain a PAF receptor antagonist, and, if present, one or more carbohydrates, in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0–8.0 range, or water.

The liquid aerosol formulation of the present invention may include, as optional ingredients, pharmaceutically acceptable carriers, diluents, solubilizing or emulsifying agents, surfactant and excipients.

The liquid aerosol formulations of the present invention will typically be used with a nebulizer. The nebulizer can be either compressed air driven or ultrasonic. Any nebulizer known in the art can be used in conjunction with the present invention such as but not limited to: Ultravent, Mallinckrodt, Inc. (St. Louis, Mo.); the Acorn II nebulizer (Marquest Medical Products, Englewood Colo.). Other nebulizers useful in conjunction with the present invention are described in U.S. Pat. Nos. 4,624,251 issued Nov. 25, 1986; 3,703,173 issued Nov. 21, 1972; 3,561,444 issued Feb. 9, 1971 and 4,635,627 issued Jan. 13, 1971.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to soya lecithin, oleic acid and sorbitan trioleate, with sorbitan trioleate preferred.

The formulations of the present embodiment may also include other agents useful for stabilization or for the regulation of osmotic pressure. Examples of the agents include but are not limited to salts, such as sodium chloride, or potassium chloride, and carbohydrates, such as glucose, galactose or mannose, and the like.

Aerosol Dry Powder Formulations

It is also contemplated that the present pharmaceutical formulation will be used as a dry powder inhaler formulation comprising a finely divided powder form of the PAF receptor antagonist, and, if present, carbohydrate or carbohydrates and a dispersant. The form of the PAF receptor antagonist, and, if present, carbohydrate, will generally be a lyophilized powder. Lyophilized forms of PAF receptor antagonist, and, if present, carbohydrates, can be obtained through standard techniques.

In another embodiment, the dry powder formulation will comprise a finely divided dry powder containing a PAF receptor antagonist, and, if present, one or more carbohydrates, a dispersing agent and also a bulking agent. Bulking agents useful in conjunction with the present formulation include such agents as lactose, sorbitol, sucrose, or mannitol, in amounts that facilitate the dispersal of the powder from the device.

The present invention will be better understood from a review of the following illustrative description presenting the details of the constructs and procedures that were followed in its development and validation.

EXAMPLE 1

In this Example, the profound effects of TNF and IL-1 on the adherence of pneumococci to target airway epithelial and vascular endothelial cells is described, and the major receptor specificity on activated cells as the PAF receptor is identified.

The adherence of *S. pneumoniae* encapsulated strain AII (serotype 2) and the isogeneic unencapsulated strain R6 to human vein endothelial cells (EC) and type II lung epithelial cells (LC) was quantitated before and after stimulation of the eukaryotic cells with IL-1 or TNF. Adherence to EC was increased ~70% by TNFα stimulation (FIG. 1). IL-1 stimulation resulted in a more modest increase in pneumococcal adherence (increase from 240 ±10 to 363 ±13 bacteria/100 EC; increase from 270 ±15 to 355 ±18 bacteria/100 LC). Adherence was not affected by the presence of a type II capsule. At an input concentration of $10^7$ cfu/ml, adherence of AII and R6 to 100 TNFα-stimulated EC was 405 ±14 and 400 ±10, respectively.

The identity of the new receptor activity was suggested by two observations. Purified pneumococcal cell wall (50 μg/ml; Tuomanen et al., 1985, J. Infect. Dis. 151: 859) competitively inhibited the enhanced pneumococcal adherence to activated EC (415 ±25 decreased to 289 ±11 bacteria/100 EC) and LC (355 ± 18 decreased to 249 ±13 bacteria/100 LC). Furthermore, the enhanced adherence was profoundly attenuated (71 and 62% decrease, respectively) upon replacement of the choline on the pneumococcal cell wall with ethanolamine by substitution of the aminoalcohol in the culture medium (Tuomanen et al., 1985, supra) (decrease from 415 ±25 to 121 ±11 bacteria/100 EC; decrease from 355 ±18 to 135 ±13 bacteria/100 LC). Choline is a critical determinant of the bioactivity of platelet activating factor (PAF) and PAF has been shown to play a particularly pronounced role in the inflammatory response during pneumococcal pneumonia and meningitis (Cabellos et al., 1992, J. Clin. Invest. 90: 612).

The direct participation of the PAF receptor in pneumococcal adhesion was suggested by the ability of two PAF receptor antagonists to virtually eliminate the enhanced adhesion of pneumococci to activated cells (FIG. 2). The PAF antagonists L659,989 (Cabellos et al., supra) and WEB 2086 (Kunz et al., 1992, J. Biol. Chem. 267: 9101) inhibited adherence at $ED_{50}$ of $5\times10^{-8}$M and $1\times10^{-8}$M, respectively. Similar $ED_{50}$ values have been reported in animal models for L659,989 (Cabellos et al., supra) and in in vitro PAF receptor transfected cells for WEB 2086 (Kunz et al., supra). Neither receptor antagonist affected pneumococcal adherence to resting EC (240 ±15 versus 224 ±12 and 237 ±9 bacteria/EC in the presence of 1 μM WEB 2086 and L659, 989, respectively) or LC (270 ±10 bacteria versus 264 ±8 and 272 ±8, respectively).

Specific receptors for PAF have been identified in numerous tissues and cells including lung and brain membranes, platelets, neutrophils, eosinophils and macrophages (Chao and Olson, 1993, Biochem. J. 292: 617). The PAF receptor is an approximately 39,000 Da protein consisting of an extracytoplasmic amino-terminal region, seven putalive membrane spanning domains, and a cytoplasmic carboxyl terminus (Chao and Olson, supra). These features are characteristic of the seven members of the rhodopsin receptor family (Kunz et al., supra). PAF receptors appear to be well conserved between species. Comparison of the human and guinea pig sequences indicate that both consist of 342 amino acids, which are organized into seven putalive membrane spanning domains and possess about 83% sequence similarity at the amino acid level (Kunz et al., supra). Unique to the human PAF receptor among this class of molecules, however, is the presence of a single glycosylation site in the putative third extracellular loop between amino acids 169 and 171 (Kunz et al., supra). PAF glycosylation sites differ in position and number in other species, for example, guinea pig PAF receptors possess two glycosylation sites; one between amino acids 169 and 171 and the second in the -N-terminal extracellular loop. The high affinity binding of PAF to PAF receptor results in transmembrane signalling, which is though to involve G-proteins and to be coupled to phospholipase A2 and phospholipase C (Chao and Olson, supra).

Recently, the PAF receptor was cloned from human leukocytes and successfully transfected into kidney epithelial cells (Kunz et al, supra). To determine if pneumococci could directly adhere to PAF receptors, human U937 cells (ATCC CRL1593; embryonic kidney epithelial cells stably transfected with the SV40 large T-antigen) and COS-7 cells (ATCC CRL 1651; monkey kidney) were transfected with the human PAF receptor cDNA (Gerard and Gerard, 1994, J. Immunol 152: 793) or the cDNA containing a Flag construct (Kunz et al., supra) by electroporation (Kunz et al., supra) or the addition of cationic liposomes (Gerard and Gerard, supra). Ligand binding to these receptors is temperature-dependent, sensitive to PAF receptor antagonists, and results in rapid internalization of the receptor, comparable to that of native receptor-bearing cells (Gerard and Gerard, supra). Controls cells were transfected with vector alone. Monolayers of transfected and control cells were prepared in 60-well Terasaki dishes. Monolayers of COS-7 and U937 cells are prepared in 48-well culture dishes using the methods previously described for EC and LC (Geelen et al., 1993, Infect. Immun. 61: 1538). Expression of PAF receptors was confirmed by immunohistochemical staining using a monoclonal antibody against the Flag-PAF receptor gene product (Kunz et al., supra).

Figure 3:
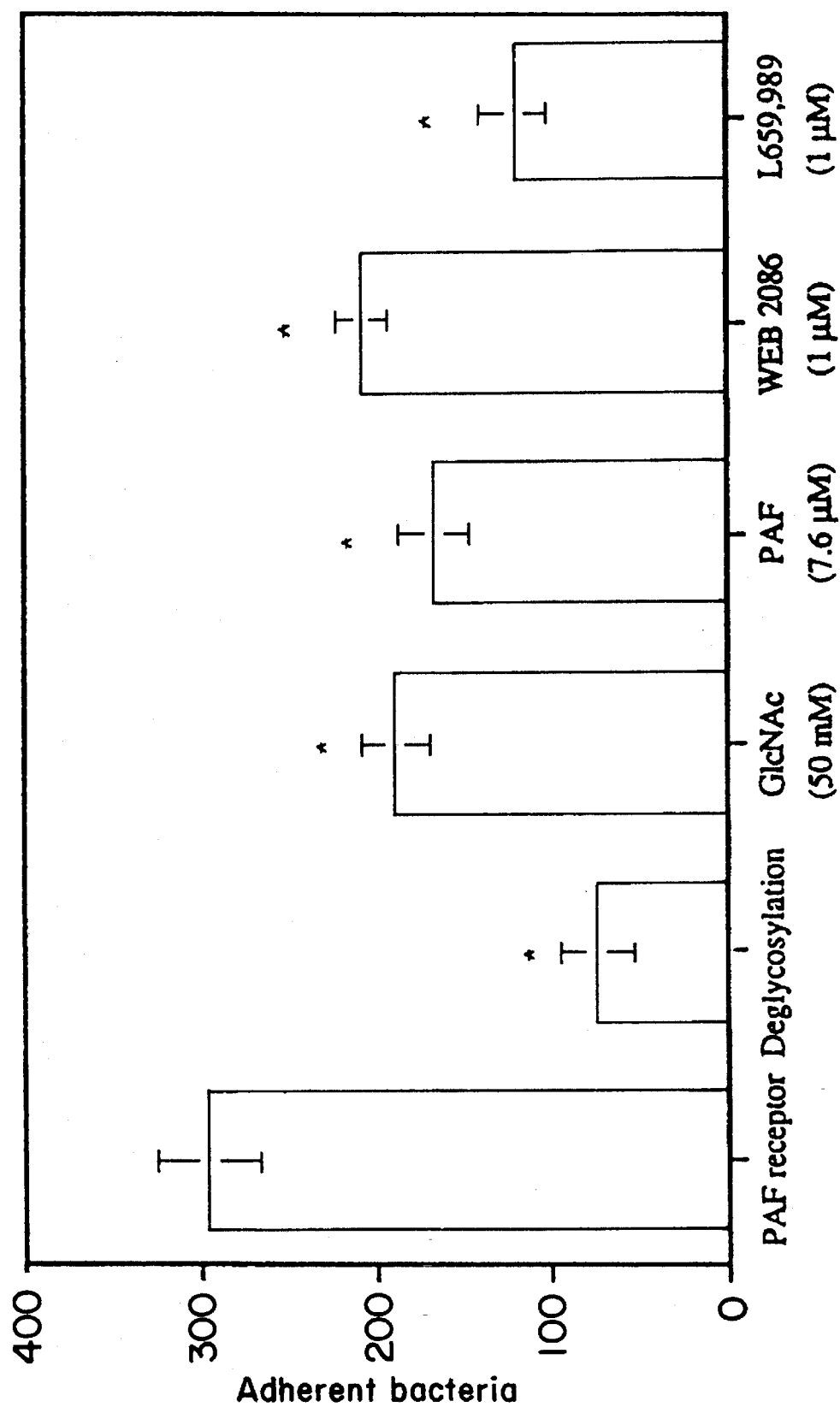
FIG. 3. Effect on pneumococcal adherence to PAF receptors of receptor deglycosylation, the antagonists WEB 2086 and L659,989 (1 μM) and removal of phosphorylcholine from the pneumococcal cell wall (Tuomanen et al., 1985, J. Infect. Dis. 151: 859).

Pneumococcal adherence to control COS-7 and U937 cells was low, probably because the kidney is not normally a target for pneumococcal infection (FIG. 3). Upon transfection of the PAF receptor into these cells, adherence increased greater than 6-fold (FIG. 3). Adherence was unaffected by the presence of a type II capsule. At an input concentration of $10^7$ cfu/ml, adherence to U937 cells by R6 and AII cells was 296 ±30 and 277 ±38, respectively. Adherence of pneumococci grown in ethanolamine was approximately 10-fold less than bacteria grown in medium containing choline. At an input concentration of $10^7$ cfu/ml, adherence to U937 cells was 25 ±10 for ethanolamine grown R6 bacteria, compared to 296 ±30 for choline grown R6 bacteria. Further confirmation that pneumococci were targeting the PAF receptor came from the ability of PAF and the PAF antagonists WEB 2086 and L659,989 to inhibit pneumococcal adherence (FIG. 3).

It was of interest to determine if pneumococci recognized PAF strictly in a choline dependent fashion or if the single glycosyl determinant of the PAF receptor contributed to receptor recognition. As noted above, the human PAF receptor differs from the PAF receptor from other species in the absence of an N-linked glycosylation site in the $NH_2$-terminal putative extracellular sequence and the presence of only one extracellular glycosylation site at positions 169–171 (Kunz et la., supra). This single glycosylation site was removed by site directed mutagenesis of the triplet amino acid glycosylation site. Non-glycosylated PAF receptor reduced pneumococcal adherence to both COS-7 and U937 cells by about 75% (FIG. 3). At an input concentration of $10^7$ cfu/ml, R6 adherence to U937 cells that expressed the non-glycosylated PAF receptor was decreased from 296 ± 30 to 74 ±20.

Figure 4A:
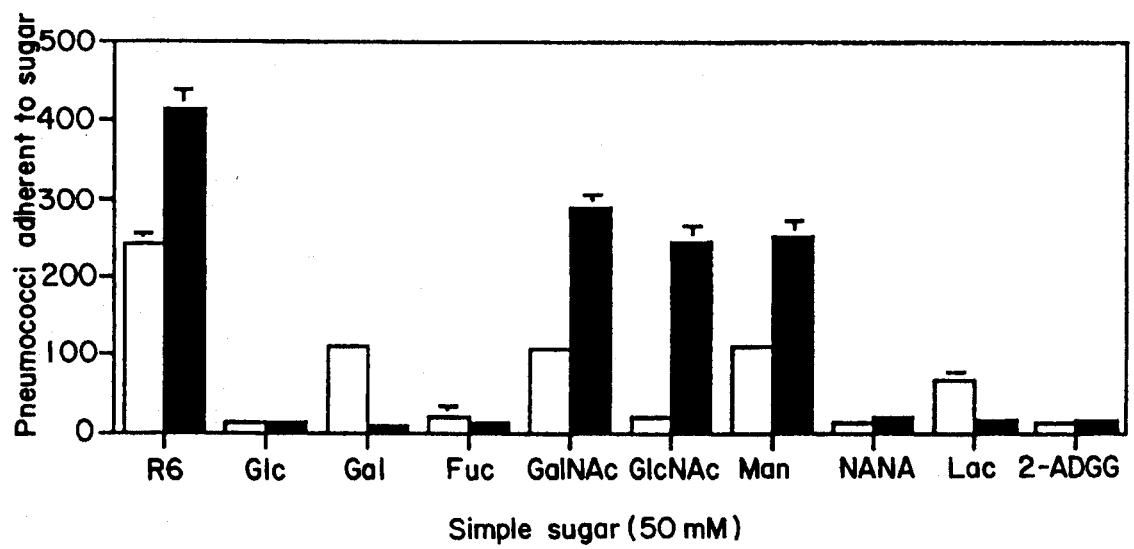
FIG. 4. Effect of simple sugars on adherence of R6 to resting and cytokine-stimulated human cultured type II pneumocytes (A) and vascular endothelial cells (B). R6 ($10^7$ cfu/ml) was exposed to various simple sugars (15 min, room temperature) and then co-incubated with either resting (□) or cytokine-stimulated (■) monolayers for 30 min. Pneumococcal adherence to a designated sugar was defined as bacterial adherence to 100 host cells in the absence of sugar–bacterial adherence to 100 host cells in the presence of sugar. Results are the means ±SD for duplicate wells in at least six independent experiments. Glc=D-glucose, Gal=D-galactose, Fuc=L-fucose, GalNAc=N-acetyl-D-galactosamine, GlcNAc=N-acetyl-D-glucosamine, Man=D-mannose, NANA=sialic acid, Lac= lactose and 2-ADGG=2-acetamido-2-deoxy-3-O-B-D-galactopyranosyl-D-galactopyranose.
Figure 4B:
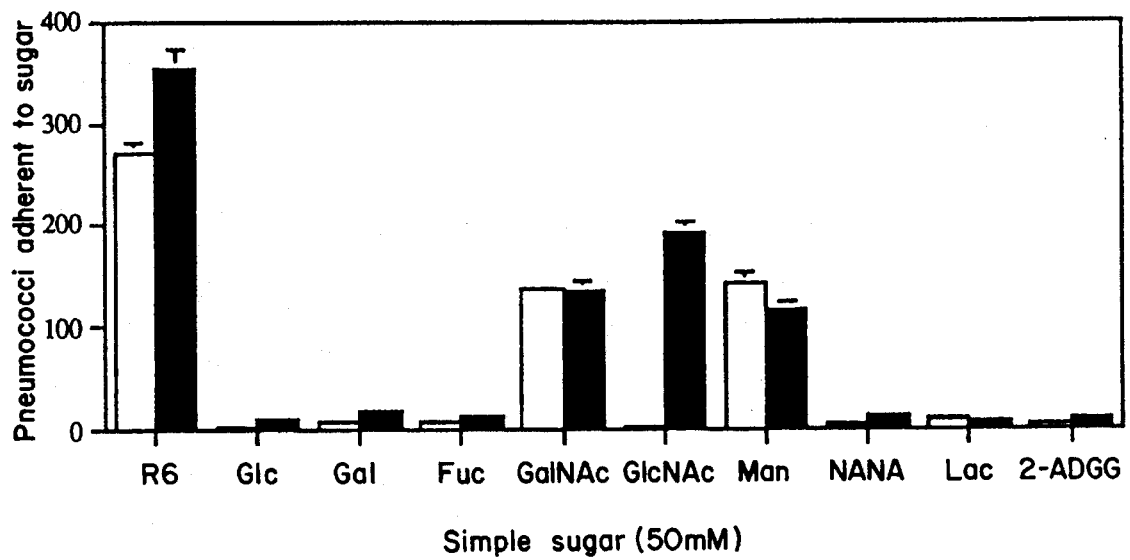

The contribution of carbohydrate recognition to pneumococcal adherence to cytokine-stimulated EC and LC was tested using competition assays performed in the presence of monosaccharides (1–50 mM) or glycoconjugates (0.003–2 mM) the role of carbohydrate recognition in pneumococcal adherence is disclosed more fully in copending application Ser. No. 08/254,577, Attorney Docket No. 600-1-084, filed Jun. 6, 1994 by Tuomanen and Cundell, entitled "MODULATORS OF PNEUMOCOCCAL ADHERENCE TO PULMONARY AND VASCULAR CELLS AND DIAGNOSTIC AND THERAPEUTIC APPLICATIONS"; hereinafter Tuomanen and Cundell. Bacteria were pre-incubated for 15 min at room temperature with final concentrations of the sugars as stated, centrifuged (3,000 rpm, 3 min) to remove unbound sugar, resuspended to $1×10^7$ cfu/ml in albumin buffer and added to the adherence assay. Comparison of the ability of single sugars (Tuomanen et al., J. Exp. Med. 168: 267), to inhibit adherence indicated that while GalNAc and D-mannose were effective in inhibiting adherence to resting cells, GlcNAc became effective in activated cells (FIG. 4). GlcNAc showed no effect on the adherence of pneumococci lacking phosphorylcholine, a finding consistent with the proposed role of choline in targeting pneumococci to the PAF receptor. Adherence of bacteria lacking choline to activated cells in the presence and absence of GlcNAc was 121 ±11 and 119 ±5/100 EC and 137 ± 7 and 135 ±13/100 LC, respectively. Pneumococcal adherence to transfected COS-7 and U937 cells was also decreased by about 40% in the presence of GlcNAc (FIG. 3).

Resting EC and LC express two classes of pneumococcal receptors: GalNAcg 1-4Gal or GalNAcβ1-3Gal on a mannose core (Tuomanen and Cundell, supra). These two receptor specificities are best defined by the inhibitory activities of the glycoconjugate asialo-GM2 for the β1-4 receptor and globoside for the β1-3 receptor. In contrast to the results with GlcNAc, however, neither globoside not asialo-GM2 decreased pneumococcal adherence to transfected PAF receptors. At an input concentration of $10^7$ cfu/ml, adherence of R6 to U937 cells in the presence of globoside and asialo-GM2 was 318 ±30 and 327 ±39, compared with 296 ±30 in the absence of the glycoconjugates.

Figure 5:
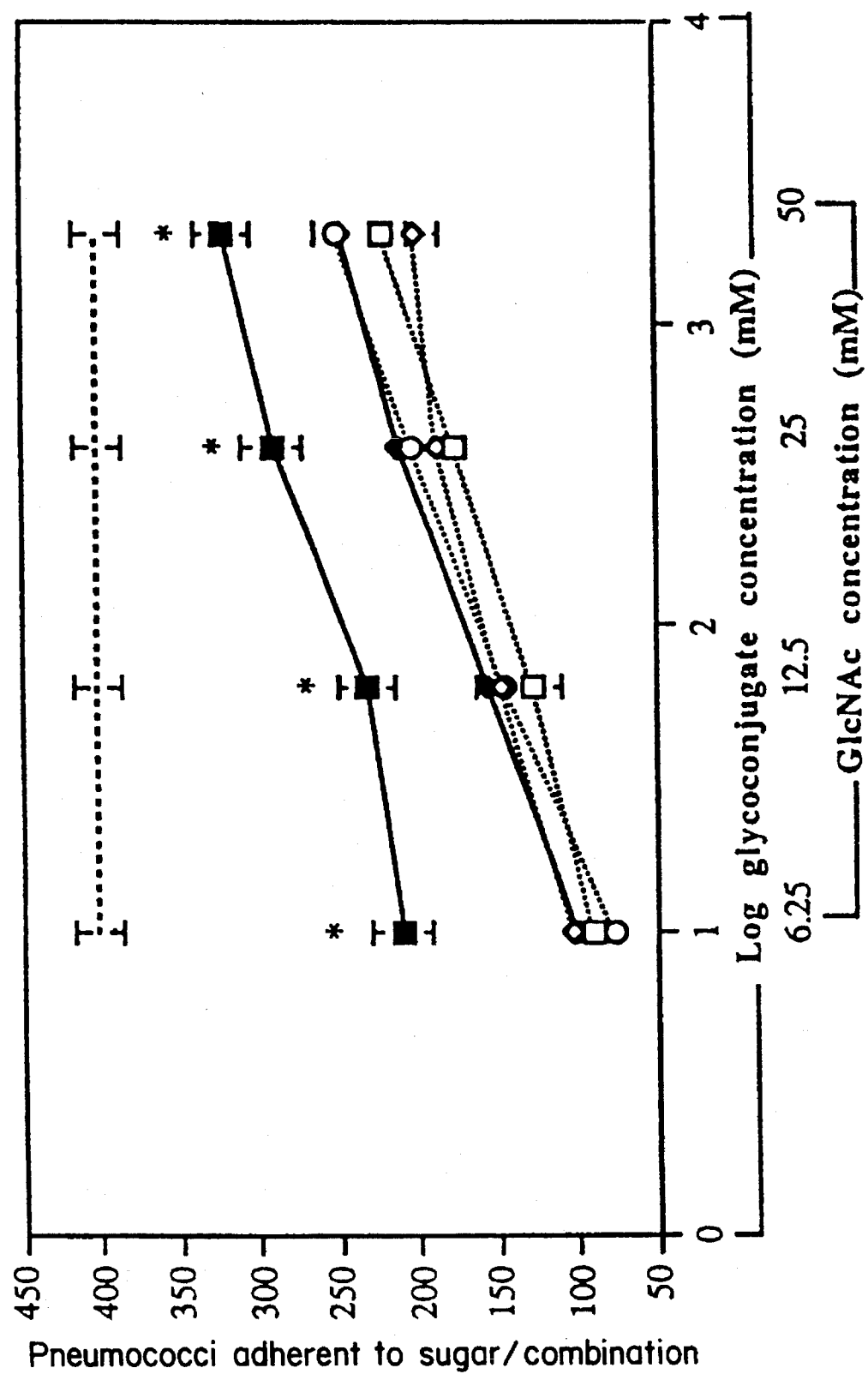
FIG. 5. Pneumococcal glycoconjugate receptors on cytokine-stimulated monolayers. The number of pneumococci adherent to the GalNAcβ1-4Gal population was defined by asialo-GM2 (□) and those adherent to the GalNAcβ1-3Gal population by globoside (◊). To define whether the carbohydrate specificities were contained in one or more receptors, the ability of two component mixtures of GlcNAc (○) plus either globoside (♦) or asialo-GM2 (■) to impair pneumococcal adherence to a greater degree than each sugar alone was assessed. Final concentrations were composed of the single sugar or equally of the 2 sugars tested. Control adherence to TNF-α-stimulated monolayers is indicated by the hatched line (-----). $*p<0.05$ compared to asialo-GM2 or GlcNAc alone. Pneumococcal adherence to each designated sugar was determined from the bacterial adherence to 100 host cells in the absence of sugar–bacterial adherence to 100 host cells in the presence of sugar. Results shown are the means ±SD for duplicate wells in at least six independent experiments.

Notwithstanding the above, cytokine stimulation of EC and LC resulted in a greater number of both of these resting cell receptors (Table 1), in addition to the appearance of the new GlcNAc specificity. This latter specificity was independent of the GalNAcβ1-4Gal specificity since the inhibitors were additive; GlcNAc was related to the GalNAcβ1-3Gal receptor population as these inhibitors were not additive (FIG. 5). If the effects of the sugars were non-additive then they were considered to occupy the same or linked receptors; if additive then they were interpreted to be present in separate receptors.

TABLE 1

Pneumococcal receptor populations on resting and cytokine-stimulated human type II lung cells (LC) and vascular endothelial cells (EC)

| | Number of pneumococci adherent to designated receptor on host cell* | | |
|---|---|---|---|
| Cell type | GalNAcβ1-4Gal | GalNAcβ1-3Gal | Control |
| EC | 140 ± 12 | 110 ± 8 | 240 ± 10 |
| EC + TNFα | 180 ± 13 | 200 ± 9 | 415 ± 25 |
| LC | 140 ± 10 | 140 ± 10 | 270 ± 15 |
| LC + IL-1α | 205 ± 9 | 200 ± 11 | 355 ± 18 |

TABLE 1-continued

Pneumococcal receptor populations on resting and cytokine-stimulated human type II lung cells (LC) and vascular endothelial cells (EC)

| Cell type | Number of pneumococci adherent to designated receptor on host cell* | | |
|---|---|---|---|
| | GalNAcβ1-4Gal | GalNAcβ1-3Gal | Control |

*R6 ($10^7$ cfu/ml) was exposed to increasing concentrations (0.003–2 mM) of either asialo-GM2 or globoside and then co-incubated with either resting or cytokine-stimulated monolayers for 30 min at 37° C. Asialo-GM2 was used to define the number of pneumococci adherent to the GalNAcβ1-4Gal population of receptors and globoside those adherent to the GalNAcβ1-3Gal population. Pneumococcal adherence to each designated sugar was determined from the bacterial adherence to 100 host cells in the absence of sugar (control values)
    - bacterial adherence to 100 host cells in the presence of sugar. Results are
    shown for the maximum (2 mM) of each sugar tested and are the means ± SD
    for duplicate wells in at least six independent experiments.

Previous studies have indicated that, although PAF receptor antagonists markedly attenuated inflammation during experimental pneumococcal pneumonia, pneumococcal teichoicated components do not activate the PAF receptor in model in vitro cell culture systems and do not prevent PAF activation of the receptor (Cabellos et al., supra). However, as shown in the following example, these studies were wrong. In fact, pneumococci appear to be potent activators of PAF receptor.

These results suggest that the PAF receptor anchors the pneumococci to the target cell in a choline- and carbohydrate-dependent fashion. This anchoring appears to lead to the triggering of a signal transduction cascade. Moreover, the PAF receptor is known to be rapidly internalized after expression on the cell surface (Gerard and Gerard, supra), suggesting this attachment may afford the bacteria with a route of migration into or across endothelial or epithelial cells. Pneumococci have been visualized within vascular endothelial cells in vitro. The ability of cells bearing the PAF receptor to take-up pneumococci was tested directly in a bacterial protection assay. In this experiment, U937 and COS-7 cells transfected with either PAF receptor or non-glycosylated PAF receptor were incubated with $10^7$ cfu/ml of R6 for 2 h at 37° C. The cells were then washed twice with Medium 199 and were treated with 50 μg/ml gentamicin for 90 min at 37° C. Gentamicin treatment destroys bacteria that are not protected by internalization in the mammalian cells. The cells were washed twice with Medium 199 and lysed by resuspension in 0.5 ml of 0.1% Triton X-100. Serial 100-fold dilutions of cell suspension were plated onto blood plates and cfu/ml determined after 24 h incubation at 37° C. Of the 1–2×$10^4$ bacteria initially adherent to a monolayer, 300 were recovered from lysates of cells treated with gentamicin for 2 hours indicating that ~3% of adherent bacteria entered the cells with time and became protected from the extracellular antibiotic. Non-glycosylation of the PAF receptor resulted in a 10-fold reduction in the number of pneumococci internalized.

We conclude that pneumococcal adherence to human type II pneumocytes and vascular endothelial cells is qualitatively and quantitatively affected by cytokine and pneumococcal activation of the target cell. This is consistent with observations of enhanced adherence of pneumococci to virally infected cells and greater susceptibility to pneumococcal disease during viral infection (Plotowski et al, Am. Rev. Respir. Dis. 134: 1040). Resting LC and EC bear two classes of receptor containing GalNAcβ1-4Gal and GalNAcβ1-3Gal. Cytokine stimulation results in receptor expansion with enhanced pneumococcal adherence being targeted to the PAF receptor. This Example reports the first time a pathogen has been found to bind to this receptor. It is also the first identification of a receptor for an adhesive ligand present in a bacterial cell wall proper, in this case, the choline-containing teichoicated species unique to the pneumococcus. The presence of choline as a bioactive determinant in both PAF and the pneumococcal teichoic acid/lipoteichoic acid suggests ligand mimicry as a basis for the targeting of pneumococci to the PAF receptor. The profound attenuation of pneumococcal inflammation in the presence of PAF receptor antagonists suggests the physiological importance of the association of pneumococci with the PAF receptor during pneumonia and introduces a novel use of PAF receptor antagonists to interfere with pneumococcal attachment to eukaryotic cells.

EXAMPLE 2

Pneumococci Activate PAF Receptor

Activation of COS-7 cells transfected with the PAF receptor was assayed. The cells were exposed to medium (control), platelet activating factor (100 mM), pneumococci ($10^8$ bacteria/ml), and ethanolamine cultured pneumococci ($10^8$ bacteria/ml). Inhibition of activation by PAF and pneumococci with the PAF receptor antagonist L659,989 (2 μg/ml) was also measured. Cellular activation was measured by detecting incorporation of $^3H$ in inositoltriphosphate (IP3).

The results of this assay are shown in FIG. 6. Very little $^3H$-labeled IP3 was detected in the control cells, or after exposure to ethanolamine-cultured pneumococci. As noted above, the ethanolamine-cultured pneumococci lack choline, and fail to bind appreciably to the PAF receptor.

As expected, PAF treatment resulted in significant $^3H$ incorporation in IP3. However, surprisingly, contacting the transfected COS cells with pneumococci produced a very strong response, with much greater $^3H$-IP3 than was observed with 100 mM PAF. Both the PAF- and pneumococcal-mediated activation could be almost completely inhibited with the PAF receptor antagonist L659,989. These results indicate that activation of COS cells by pneumococci proceeds via the PAF receptor. The failure of ethanolamine-cultured bacteria to activate the receptor further indicates a role for teichoic acid in binding to and activation of PAF receptor.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

Various references are cited throughout this specification, each of which is incorporated herein by reference in its entirety.

What is claimed is:

1. A method for preventing or treating an infection with *Streptococcus pneumoniae* comprising administering to a subject believed to be in need of such treatment an amount of an antagonist of platelet activating factor receptor effective to inhibit binding of *S. pneumoniae* to host cells.

2. The method according to claim 1, further comprising administering an amount of carbohydrate containing an N-acetyl-D-glucosamine motif effective to inhibit binding of *S. pneumoniae* to host cells.

3. The method according to claim 2, further comprising administering an amount of a second carbohydrate selected from the group consisting of a carbohydrate containing a disaccharide N-acetyl-D-galactosamine β1-4Gal motif, a disaccharide N-acetyl-D-galactosamine β1-3Gal motif, and a mixture thereof, effective to inhibit binding of *S. pneumoniae* to host cells.

4. The method according to claim 1, in which the antagonist of platelet activating factor receptor is selected from the group consisting of L659,989, L652,731, WEB 2086, kadsurenone, and FR72112.

5. The method according to claim 2, in which the carbohydrate is N-acetyl-D-glucosamine.

6. The method according to claim 3, in which the second carbohydrate is selected from the group consisting of forssman glycolipid, globoside, asialo-GM1 and asialo-GM2.

7. The method according to claim 1, 2, or 3, further comprising administering an amount of a carbohydrate selected from the group consisting of mannose, N-acetyl-galactose, mannose-D-mannose, and methyl-α-D-mannopyranoside effective to inhibit binding of *S. pneumoniae* to host cells.

8. The method according to claim 2 or 3, in which the carbohydrate or carbohydrates are multivalent.

9. The method according to claim 1, 2, or 3, in which the administering comprises atomizing and inhaling.

10. The method according to claim 9, in which the atomizing is nebulizing.

11. The method according to claim 1, 2, or 3, in which the administering comprises injecting intravenously.

12. The method according to claim 1, further comprising administering an inhibitor of inflammation effective to inhibit expression of platelet activating factor receptor.

13. The method according to claim 12, wherein the inhibitor of inflammation is selected from the group consisting of a neutralizing antibody to tumor necrosis factor, a neutralizing soluble tumor necrosis factor receptor, a neutralizing antibody to interleukin-1, and a neutralizing soluble interleukin-1 receptor.

14. A pharmaceutical composition comprising an amount of a platelet activating factor receptor antagonist effective to inhibit binding of *S. pneumoniae* to host cells, an amount of a carbohydrate containing an N-acetyl-D-glucosamine motif effective to inhibit binding of *S. pneumoniae* to host cells, and a pharmaceutically acceptable carrier.

15. The pharmaceutical composition of claim 14, further comprising an amount of a carbohydrate selected from the group consisting of a carbohydrate containing a disaccharide N-acetyl-D-galactosamine β1-3Gal motif and a carbohydrate containing a disaccharide N-acetyl-D-galactosamine β1-4Gal motif effective to inhibit binding of *S. pneumoniae* to host cells.

16. The pharmaceutical composition of claim 14, in which the antagonist of platelet activating factor receptor is selected from the group consisting of L659,989, L652,731, WEB 2086, kadsurenone, and FR72112.

17. The pharmaceutical composition of claim 14, in which the carbohydrate is N-acetyl-D-glucosamine.

18. The pharmaceutical composition of claim 15, in which the second carbohydrate is selected from the group consisting of forssman glycolipid, globoside, asialo-GM1 and asialo-GM2.

19. The pharmaceutical composition of claim 14 or 15, further comprising an amount of a carbohydrate selected from the group consisting of mannose, N-acetyl-galactose, mannose-D-mannose, and methyl-α-D-mannopyranoside effective to inhibit binding of *S. pneumoniae* to host cells.

20. The pharmaceutical composition according to claim 14 or 15, in which the carbohydrate or carbohydrates are multivalent.

21. The pharmaceutical composition of claim 14 or 15, in which the pharmaceutical composition is an aerosol formulation, which formulation contains a dispersant.

22. The pharmaceutical composition of claim 21, in which the dispersant is a surfactant.

23. The pharmaceutical composition of claim 21, which is a dry powder aerosol formulation, in which the carbohydrate or carbohydrates are present in finely divided powder.

24. The pharmaceutical composition of claim 23, which further comprises a bulking agent.

25. The pharmaceutical composition of claim 21, which is a liquid aerosol formulation further comprising a pharmaceutically acceptable diluent.

26. The pharmaceutical composition of claim 25, in which the diluent is selected from the group consisting of sterile water, saline, buffered saline, and dextrose solution.

27. The pharmaceutical composition of claim 14 or 15, in which the host cell is selected from the group consisting of lung epithelial cells and vascular endothelial cells.

* * * * *